(12) United States Patent
Hadba et al.

(10) Patent No.: US 8,829,129 B2
(45) Date of Patent: *Sep. 9, 2014

(54) WATER-SWELLABLE COPOLYMERS AND ARTICLES AND COATINGS MADE THEREFROM

(75) Inventors: Ahmad R. Hadba, Middlefield, CT (US); Brian Cuevas, Cumming, GA (US); Frank R. Schiretz, Middletown, CT (US); Joshua Stopek, Guilford, CT (US)

(73) Assignee: Covidien LP, Mansfield, MA (US)

(*) Notice: Subject to any disclaimer, the term of this patent is extended or adjusted under 35 U.S.C. 154(b) by 66 days.

This patent is subject to a terminal disclaimer.

(21) Appl. No.: 13/300,906

(22) Filed: Nov. 21, 2011

(65) Prior Publication Data

US 2012/0065676 A1 Mar. 15, 2012

Related U.S. Application Data

(62) Division of application No. 13/069,994, filed on Mar. 23, 2011, now Pat. No. 8,083,771, which is a division of application No. 13/070,017, filed on Mar. 23, 2011, now Pat. No. 8,092,492, which is a division of application No. 11/660,566, filed as application No. PCT/US2005/029094 on Aug. 16, 2005, now Pat. No. 7,935,773.

(60) Provisional application No. 60/602,689, filed on Aug. 19, 2004.

(51) Int. Cl.

| C08F 220/06 | (2006.01) |
|---|---|
| A61L 31/04 | (2006.01) |
| C08F 220/38 | (2006.01) |
| A61L 17/10 | (2006.01) |
| A61L 24/04 | (2006.01) |
| C08L 33/14 | (2006.01) |
| A61B 17/064 | (2006.01) |
| A61B 17/06 | (2006.01) |
| C08F 220/58 | (2006.01) |
| A61B 17/00 | (2006.01) |

(52) U.S. Cl.

CPC ............. *A61L 24/043* (2013.01); *A61L 31/041* (2013.01); *C08F 220/38* (2013.01); *A61L 17/10* (2013.01); *A61L 2400/04* (2013.01); *C08L 33/14* (2013.01); *C08F 220/06* (2013.01); *A61B 2017/00898* (2013.01); *A61B 17/064* (2013.01); *A61B 17/06166* (2013.01); *C08F 220/58* (2013.01)

USPC ........... 526/240; 428/394; 428/395; 606/151; 606/157; 606/219; 606/233; 526/287; 526/303.1

(58) Field of Classification Search

CPC ............ A61B 17/06166; A61B 17/064; A61L 17/10; A61L 24/041; A61L 24/043; C08F 220/06; C08F 220/38; C08F 220/58; C08L 33/04; C08L 33/14

USPC .......... 606/151, 157, 219, 233; 428/392, 394, 428/395

See application file for complete search history.

(56) References Cited

U.S. PATENT DOCUMENTS

| 3,929,741 | A | 12/1975 | Laskey | |
|---|---|---|---|---|
| 4,470,416 | A | 9/1984 | Kafrawy et al. | |
| 4,563,290 | A | 1/1986 | Okada et al. | |
| 4,610,305 | A | 9/1986 | Martin et al. | |
| 4,792,343 | A | 12/1988 | Hawe et al. | |
| 6,271,278 | B1 * | 8/2001 | Park et al. | 521/150 |
| 6,395,804 | B1 | 5/2002 | Rao et al. | |
| 6,447,798 | B1 | 9/2002 | Munro et al. | |
| 7,479,521 | B2 | 1/2009 | Braun et al. | |
| 7,935,773 | B2 * | 5/2011 | Hadba et al. | 526/287 |
| 8,083,771 | B2 * | 12/2011 | Hadba et al. | 606/233 |
| 8,092,492 | B2 * | 1/2012 | Hadba et al. | 606/219 |
| 2003/0054024 | A1 | 3/2003 | Munro et al. | |

FOREIGN PATENT DOCUMENTS

| EP | 0831169 A2 | 3/1998 |
|---|---|---|
| EP | 0831169 A2 | 3/1998 |
| EP | 1918310 A1 | 5/2008 |
| FR | 2830867 A1 | 4/2003 |
| FR | 2910899 A1 | 7/2008 |
| SU | 1402349 A | 1/1982 |
| WO | WO 98/51408 A | 11/1998 |
| WO | WO 98/51408 A | 11/1998 |
| WO | WO 03/033553 A1 | 4/2003 |
| WO | WO 2006/036269 A2 | 4/2006 |

OTHER PUBLICATIONS

European Search Report for EP 10003700.1 date of completion is Aug. 5, 2010 (3 pages).

Schwarz, Alexander et al., "Transcatheter Embolization Using Degradable Crosslinked Hydrogels", BioMaterials 25 (2004) 5209-5215 CODEN: Bimadu; ISSN: 0142-9612, 2004. XP002595408.

European Search Report for EP 05787818.3-2109 date of completion is Mar. 31, 2008 (7 pages).

(Continued)

Primary Examiner — Edward Cain

(57) ABSTRACT

The present disclosure relates to compositions comprising a copolymer that includes a first monomer and a second monomer that is different from the first monomer, wherein both the first and second monomer are selected from the group consisting of 3-sulfopropyl acrylate potassium salt, sodium acrylate, N-(tris(hydroxyl methyl)methyl)acrylamide, and 2-acrylamideo-2-methyl-1-propane sulfonic acid. The present disclosure further relates to methods for preparing the copolymer compositions and shaped articles comprising the copolymers.

11 Claims, 2 Drawing Sheets

(56) References Cited

OTHER PUBLICATIONS

WO 2006/029094 Search report date of Mailing Dec. 13, 2005.
European Search Report for EP 09013405.7-2109 date of completion is Mar. 5, 2010 (7 pages).
European Search Report for EP 10003701.9-2109 date of completion is May 20, 2010 (4 pages).
Delorme, Nicolas et al.: "Surface Immobilization and Mechanical Properties of Catanionic Hollow Faceted Polyhedrons" Journal of Physical Chemistry B, 110(4), 1752-1758 Coden: JPCBFK; ISSN: 1520-6106, 2006, XP002582740.

* cited by examiner

WATER-SWELLABLE COPOLYMERS AND ARTICLES AND COATINGS MADE THEREFROM

CROSS-REFERENCE TO RELATED APPLICATIONS

This application is a divisional of U.S. application Ser. No. 13/069,994 filed Mar. 23, 2011, now U.S. Pat. No. 8,083,771 which is a divisional of U.S. application Ser. No. 13/070,017 filed Mar. 23, 2011, now U.S. Pat. No. 8,092,492 which is a divisional of U.S. application Ser. No. 11/660,566 filed Sep. 7, 2007, now U.S. Pat. No. 7,935,773 which is a 371 of PCT/US2005/029094 filed Aug. 16, 2005, which claims priority to U.S. Provisional Application No. 60/602,689 filed Aug. 19, 2004, and the disclosures of each of the above-identified applications are hereby incorporated by reference in their entirety.

TECHNICAL FIELD

This disclosure relates, generally, to the medical arts. More particularly, it relates to devices and compositions for sealing openings in tissue.

BACKGROUND OF RELATED ART

Openings may be formed in tissue by numerous means. For example, an opening in tissue may be created intentionally during a medical procedure (e.g., via use of a needle, trocar, scalpel, etc.) or may be accidentally created through trauma. In general, the existence of an opening in tissue over time is undesirable and requires closure.

Many techniques have been developed for the surgical closing of openings. Sutures were invented long ago, for example. Typically, if a suture is used to close an opening in tissue, a smaller opening typically remains as a result of the fact that the passage of the needle through tissue creates an opening having the same diameter as the needle which opening is not fully occupied by the suture which is typically of a smaller diameter than the needle. Thus, leaking at the site of suturing may arise in some applications.

Another technique for closing openings in tissue includes the use of staples. As those skilled in the art will appreciate, the application of staples may result in smaller openings being formed at the site of staple application as the legs of the staples pass through tissue.

It would be advantageous to provide means for easily and reliably closing openings in tissue, without leaving additional openings, however small.

SUMMARY

Compositions in accordance with this disclosure are water-swellable and can thus be used to close openings in tissue. The compositions include a copolymer containing repeating units of two or more monomers selected from the group consisting of 3-sulfopropyl acrylate potassium salt ("KSPA"), sodium acrylate ("NaA"), N-(tris(hydroxyl methyl)methyl)acrylamide ("tris acryl"), and 2-acrylamido-2-methyl-1-propane sulfonic acid (AMPS). The compositions can formed into a desired shape or may be used to coat at least a portion of a medical device, such as a hernia mesh, suture or surgical staple. After being dried, the copolymer will swell upon contact with moisture, such as blood or other bodily fluid.

BRIEF DESCRIPTION OF DRAWINGS

For a fuller understanding of the subject matter described herein, reference should be made to the following detailed description, taken in connection with the accompanying diagrammatic drawings, in which.

DETAILED DESCRIPTION OF PREFERRED EMBODIMENTS

Figure 1:
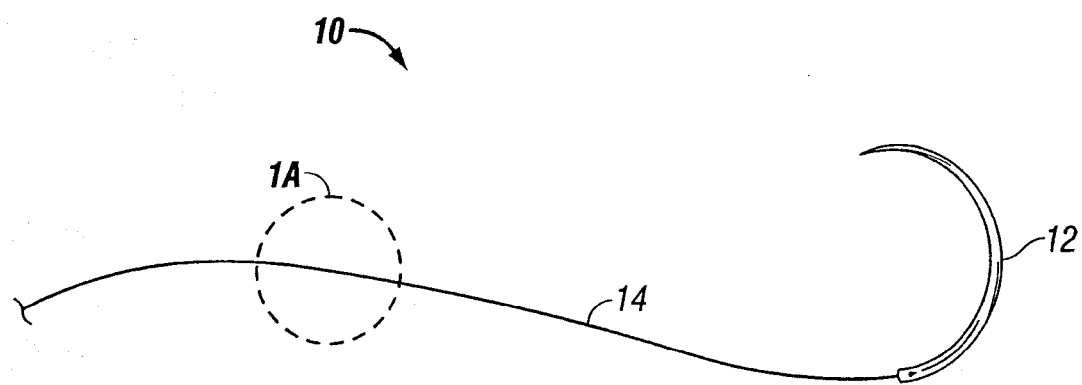
FIG. 1 shows a suture having a coating of a water-swellable composition in accordance with this disclosure.
Figure 1A:
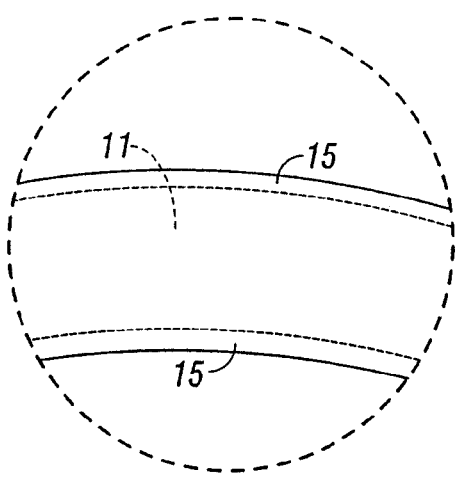

Water-swellable compositions are described herein that are useful in closing openings in tissue. The compositions include a copolymer containing repeating units of two or more monomers selected from the group consisting of 3-sulfopropyl acrylate potassium salt ("KSPA"), sodium acrylate ("NaA"), N-(tris(hydroxyl methyl)methyl)acrylamide ("tris acryl"), and 2-acrylamido-2-methyl-1-propane sulfonic acid (AMPS). Thus, the copolymer includes a first monomer and a second monomer that is different from the first monomer, wherein both the first and second monomer are selected from the group consisting of 3-sulfopropyl acrylate potassium salt ("KSPA"), sodium acrylate ("NaA"), N-(tris(hydroxyl methyl)methyl)acrylamide ("tris acryl"), and 2-acrylamido-2-methyl-1-propane sulfonic acid (AMPS). The first monomer can be from 5 to 95 percent of the total monomer used to form the copolymer and the second monomer can be from 95 to 5 percent of the total monomer used to form the copolymer. In particularly useful embodiments, the first monomer can be from 25 to 75 percent of the total monomer used to form the copolymer and the second monomer can be from 75 to 25 percent of the total monomer used to form the copolymer. Another embodiment includes homopolymers derived from KSPA, NaA, trisacryl and AMPS. It is further contemplated that the composition may include hydrophilicity modifying monomers copolymerizable therewith. Suitable hydrophilicity modifying monomers include but are not limited to methylmethacrylate, butylacrylate, cyclohexylacrylate, styrene, styrene sulphonic acid, etc.

The copolymer may be crosslinked. A suitable crosslinker, if present, is, for example, a low molecular weight di- or polyvinylic crosslinking agent such as ethylenglycol diacrylate or dimethacrylate, di-, tri- or tetraethylen-glycol diacrylate or dimethacrylate, allyl(meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or -bismethacrylamide, ethylene bisacrylamide or ethylene bismethacrylamide, triallyl phthalate or diallyl phthalate. The average weight average molecular weight of the crosslinker is, for example, up to 1000, preferably up to 750 and most preferably up to 500. A particularly useful crosslinking agent is N,N'methylenebisacrylamide ("MBAA"). When used, a crosslinking agent may be used in amounts from 0.1 to 20 percent by weight of the copolymer, more preferably from 0.1 to 10 percent by weight of the copolymer.

The copolymer may be formed using any technique within the purview of one skilled in the art. Suitable polymerization conditions will be apparent to those skilled in the art, given the particular starting materials chosen. In certain embodiments, the copolymer is prepared with the use of polymerization initiator. Suitable polymerization initiators are typically those that are initiating a radical polymerization of ethylenically unsaturated compounds. The radical polymerization may be induced thermally or by radiation (e.g., UV, visible, IR, γ, E-beam and the like). In particularly useful embodiments, UV or visible light is used to induce polymerization. Redox initiation may also be used.

Suitable thermal polymerization initiators are known to the skilled artisan and include for example peroxides, hydroperoxides, azobis(alkyl- or cycloalkylnitriles), persulfates, percarbonates or mixtures thereof. Examples are benzoylperoxide, tert-butyl peroxide, tert-butylperoxybenzoate, di-tert-butyl-diperoxyphthalate, tert-butyl hydroperoxide, 2,2'-azobisisobutyronitrile, 1,1'-azobis(cyclohexanecarbonitrile), 4,4'-azobis(4-cyanovaleric acid) and the like.

Initiators for the radiation-induced polymerization, so-called photoinitiators, fall into two groups based on the photochemical processes that lead to the production of radicals. These two groups are α-cleavage photoinitiators and hydrogen abstraction photoinitiators. Examples of α-cleavage initiators include benzoin ethers, hydroxy alkyl phenyl ketones, dialkoxy acetophenones, methyl thiophenyl morpholino ketones, phosphine oxide derivatives, morpholino phenyl amino ketones and benzoyl cyclonexanol. Examples of H-abstraction initiators include benzophenones, thioxanthones, benzyls, camphorquinones and ketocoumarins.

Water soluble photoinitiators are particularly useful in this application. These are typically prepared by introducing water solubilizing groups onto the backbone of the initiator such that they do not significantly alter the activity of the initiator. These groups include quaternary ammonium salts, sulfonate groups, thiosulfate groups, carboxylic acid groups or hydrophilic chains. Some useful water soluble initiators are based on benzophenones, thioxanthones, benzyls, hydroxyl alkyl ketones, benzoyl methyl thiosulfate and phenyl trimethyl benzoyl phosphinates. See generally, J. P. Fouassier, *Photoinitiator Polymerization and Photocuring: Fundamentals and Applications*, Hanson/Gardner Publications, Inc., 1995. Useful photoinitiators include for example benzophenones substituted with an ionic moiety, a hydrophilic moiety or both such as 4-trimethylaminomethyl benzophenone hydrochloride or benzophenone sodium 4-methanesulfonate; benzoin $C_1$-$C_4$ alkyl ether such as benzoin methyl ether; thioxanthones substituted with an ionic moiety, a hydrophilic moiety or both such as 3-(2-hydroxy-3-trimethylaminopropoxy)thioxanthone hydrochloride, 3-(3-trimethylaminopropoxy)thioxanthone hydrochloride, thioxanthone 3-(2-ethoxysulfonic acid) sodium salt or thioxanthone 3-(3-propoxysulfonic acid) sodium salt; or phenyl ketones such as 1-hydroxycyclohexylphenyl ketone, (2-hydroxy-2-propyl)(4-diethylene glycol phenyl)ketone, (2-hydroxy-2-propyl)(phenyl-4-butanecarboxylate)ketone; or commercial products such as those available under the tradenames Darocure® or Irgacure®. Using such initiators, copolymers may be polymerized in situ by long wavelength ultraviolet light or by light of about 514 nm, for example. It is known in the art of photopolymerization to use a wavelength of light which is appropriate for the activation of a particular initiator. Light sources of particular wavelengths or bands are well-known and are commercially available from a variety of sources.

The polymerization initiator can be present in an amount of, for example, 0.05 to about 5% by weight, based on the entire amount of monomer used. A particularly useful photoinitiator is 2-hydroxy-1-(4-(2-hydroxyethoxy)-2-methyl-1-propanone ("HEMP") available from Ciba Specialty Chemicals under the tradename IRGACURE® 2959. In such embodiments, an aqueous solution containing the monomers (and optionally a crosslinking agent) and the photoinitiator is prepared. The solution is then exposed to a suitable radiation source, such as a UV lamp, to effectuate polymerization.

Prior to exposure to a radiation source, the solution may be poured onto a surface so that upon polymerization a sheet is formed. Alternatively, the solution may be poured into a mold to achieve any desired shape upon polymerization.

In another embodiment, the solution is coated onto at least a portion of the surface of a medical device prior to polymerization. Medical devices onto which the present compositions may be applied include but are not necessarily limited to: orthopedic pins, clamps, screws and plates; clips; staples; hooks; plugs; buttons; snaps; screws; anchors; anastomosis rings; prosthetic devices; bone substitutes such as mandible prostheses; needles; non-permanent intrauterine devices such as spermicides; drug delivery devices; temporary draining or testing tubes or capillaries; surgical instruments; vascular and ocular implants or supports; vertebral discs; fibrillar products, knitted or woven, and including velours, such as burn dressings; hernia patches; absorbent paper or swabs; medicated dressings; facial substitutes; gauze, fabric, sheet, felt, foam or film or gel or particles or sponge for hemostasis, as, e.g., of the liver or other internal organs; gauze bandages; and dental packs. Other products include flake or powder for burns or abrasions; foam as a resorbable prosthesis; wire substitutes in fixations; and film sprays for prosthetic devices. The present compositions may be used alone or in combination with other materials to produce products including those listed hereinabove, as well as composite products such as reinforced bone pins, needles, arterial grafts or substitutes and the like.

Optionally, therapeutically beneficial compounds may be incorporated into the present compositions, and, after application or implantation of the article or coated device, released therefrom. The biologically-active agent may be soluble in the polymer solution to form a homogeneous mixture, or insoluble in the polymer solution to form a suspension or dispersion. Over time, the biologically-active agent is released from the article or coated device into the adjacent tissue fluids, preferably at a controlled rate. The release of the biologically-active agent from the present composition may be varied, for example, by the solubility of the biologically-active agent in an aqueous medium, the distribution of the agent within the composition, ion exchange, pH of the medium, the size, shape, porosity, solubility and biodegradability of the article or coating, and the like.

The term "therapeutically beneficial compound" encompasses therapeutic agents, such as drugs, and also genetic materials and biological materials. A variety of therapeutically beneficial compounds may be included, including passively-functioning materials such as hyaluronic acid, as well as active agents such as growth hormones. All of the common chemical classes of such agents are included: proteins (including enzymes, growth factors, hormones and antibodies), peptides, organic synthetic molecules, inorganic-compounds, natural extracts, nucleic acids (including genes, telomerase inhibitor genes, antisense nucleotides, ribozymes and triplex forming agents), lipids and steroids, carbohydrates (including heparin), glycoproteins, polymeric drugs, e.g. polysalicilic acid, prodrugs, and combinations thereof. The agents to be incorporated can have a variety of biological activities, such as vasoactive agents, neuroactive agents, hormones, anticoagulants, immunomodulating agents, cytotoxic agents, antibiotics, antivirals, or may have specific binding properties such as antisense nucleic acids, antigens, antibodies, antibody fragments or a receptor. Proteins including antibodies or antigens can also be delivered. Proteins are defined as consisting of 100 amino acid residues or more; peptides are less than 100 amino acid residues. Unless otherwise stated, the term protein refers to both proteins and peptides. Examples include insulin and other hormones.

Specific materials include antibiotics, antivirals, antiinflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants and/or antithrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator (TPA) and anisoylated plasminogen activator (TPA) and anisoylated plasminogen-streptokinase activator complex (APSAC), colchicine and alkylating agents, and aptomers. Specific examples of modulators of cell interactions include interleukins, platelet derived growth factor, acidic and basic fibroblast growth factor (FGF) transformation growth factor β (TGF β) epidermal growth factor (EGF), insulin-like growth factor, and antibodies thereto. Specific examples of nucleic acids include genes and cDNAs encoding proteins, expression vectors, antisense and other oligonucleotides such as ribozymes which can be used to regulate or prevent gene expression. Specific examples of other bioactive agents include modified extracellular matrix components or their receptors, and lipid and cholesterol sequestrants. Examples of proteins further include cytokines such as interferons and interleukins, poetins, and colony-stimulating factors. Carbohydrates include sialylated carbohydrate ligand (sialyl-Lewis X), a structure found on neutrophil cell-surface glycoproteins and glycolipids which has been shown to bind to receptors for selectins to inhibit inflammation. A "Deliverable growth factor equivalent" (abbreviated DGFE), a growth factor for a cell or tissue, may be used, which is broadly construed as including growth factors, cytokines, interferons, interleukins, proteins, colony-stimulating factors, gibberellins, auxins, and vitamins; further including peptide fragments or other active fragments of the above; and further including vectors, i.e., nucleic acid constructs capable of synthesizing such factors in the target cells, whether by transformation or transient expression; and further including effectors which stimulate or depress the synthesis of such factors in the tissue, including natural signal molecules, antisense and triplex nucleic acids, and the like. Exemplary DGFE's are vascular endothelial growth factor (VEGF), endothelial cell growth factor (ECGF), basic fibroblast growth factor (bFGF), bone morphogenetic protein (BMP), and platelet derived growth factor (PDGF), and DNA's encoding for them. Exemplary clot dissolving agents are tissue plasminogen activator, streptokinase, urokinase and heparin. Drugs having antioxidant activity (i.e., destroying or preventing formation of active oxygen) may be used, which are useful, for example, in the prevention of adhesions. Examples include superoxide dismutase, or other protein drugs include catalases, peroxidases and general oxidases or oxidative enzymes such as cytochrome P450, glutathione peroxidase, and other native or denatured hemoproteins; anti-inflammatory agents such as glucocorticoids, betamethasone, dexamethasone, prednisolone, corticosterone, budesonide, estrogen, sulfasalazine, and mesalamine; antineoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vasodilating agents; and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril. Other therapeutically beneficial compounds are known in the art, as described in Pharmaceutical Sciences, by Remington, 14th Ed., Mack Publishing Co. (1979); The Drug The Nurse. The Patient, Including Current Drug Handbook, by Falconer et al., Saunder Company (1974-76); and Medicinal Chemistry, 3rd Ed., Vol. 1 and 2, by Burger, Wiley-Interscience Co.

The compositions of this disclosure may also optionally include a contrasting agent to facilitate detection of the article or coated medical device by imaging means such as magnetic resonance imaging, ultrasound, Doppler, and roentgenological means including x-ray, CT scan, mammography, and fluoroscopy. Alternatively, the composition may optionally include a radioactive substance detectable by a radiation detecting means including a gamma counter and a scintillation counter.

It is contemplated that it may be desirable to include a dye in the present compositions in order to increase visibility in the surgical field. Dyes known to be suitable for incorporation in medical devices can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979).

After the polymerization of the composition, the resulting shaped article or coated medical device is preferably dried, packaged in materials which are not moisture-permeable, and sterilized before use under clinical conditions. Drying can be accomplished by vacuum-drying of the apparatus under conditions well known in the art. After drying, the apparatus can be heat-sealed inside a moisture-proof material (e.g., foil laminate), and sterilized, for example, by γ-radiation, or other means, to sterilize the article or coated medical device. The device can be stored and shipped thereafter.

Articles or coated medical devices made in accordance with the present disclosure can be used in a variety of ways to close an opening in tissue. For example, a delivery catheter having a dehydrated article formed from of the present water-swellable composition can be positioned in the lumen of the catheter and introduced to the site of the opening in tissue. The dehydrated article can then be pushed from the lumen of the catheter into the opening and the catheter withdrawn from the site. The article expands upon being hydrated by natural fluids present at the site. The expansion holds the article in place and serves to seal the opening.

In another embodiment, a suture is formed at least in part of the present water-swellable composition. For example, a conventional suture (either bioabsorbable or nonbioabsorbable; monofilament or multifilament), may be coated with a composition in accordance with this disclosure and used in the same way as the conventional suture. FIG. 1 depicts a suture-needle combination 10 that includes a needle 12 and an elongate thread of suture material 14 formed at least in part of a composition in accordance with this disclosure. The suture 14 is adapted to be pulled by a needle 12 to sew closed an opening in tissue. The suture can have a diameter slightly less than a diameter of the needle, there being a clearance space about the suture equal in diameter to the diameter of the needle less the diameter of the suture. Due to the presence of coating 15 made from the present water-swellable composition on the underlying suture 11 (in this case a monofilament), the suture expands upon contact with moisture that is naturally present in bodily fluid until the suture seals the clearance space. Thus, the body's natural moisture, in most applications, will advantageously cause the suture or the suture coating to expand to fill the space around it created by the larger diameter of the needle. This eliminates the need to apply an adhesive over the sutures and thus eliminates the step of curing the adhesive.

Figure 2:
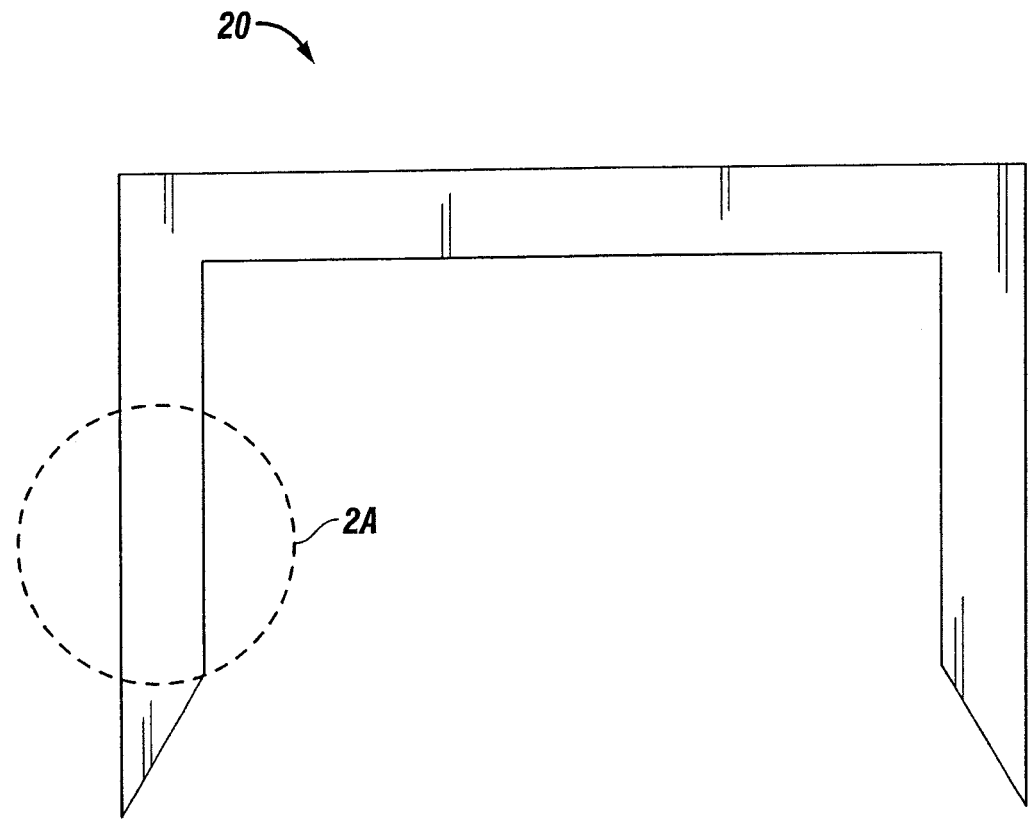
FIG. 2 shows a staple having a coating of a water-swellable composition in accordance with this disclosure.
Figure 2A:
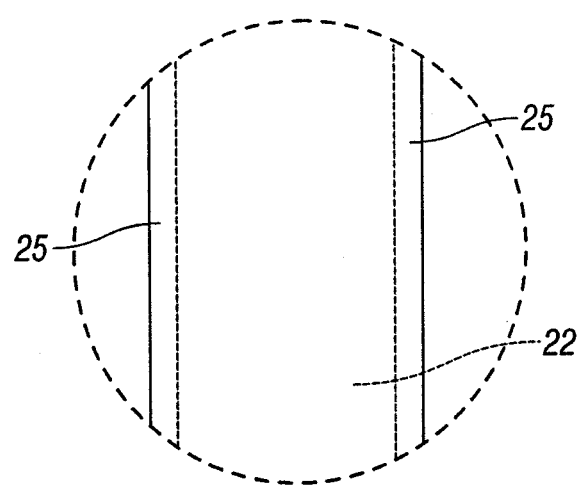

In another embodiment shown in FIG. 2, coated staple 20 is shown. As seen therein, a rigid medical staple 22 is coated with a composition in accordance with this disclosure. Due to the presence of coating 25 made from the present water-swellable composition, the staple expands upon contact with moisture that is naturally present in bodily fluid until any openings made by the stapling procedure are filled.

In yet another embodiment, the present compositions are used to provide hemostasis. It is contemplated, for example, that dried sheets of the present copolymers can be ground to a suitable particle size (e.g., 10-1,000 μm) and sprinkled as a dry powder onto a bleeding or otherwise oozing wound. The particles absorb liquid, swell and rapidly stop the bleeding. It is further contemplated that the present water-swellable copolymer compositions can be coated onto particles of suitable size and the coated particles dehydrated. The particles may be made from any biocompatible material that is either absorbable or non-absorbable by the body. Non-limiting examples of suitable materials from which the particles can be made include silica, polysaccharides (for example, crosslinked dextran such as Sephadex beads, hyaluronic acid, aliginate, carboxy methyl cellulose, ionically modified dextrans, e.g. sulfonated or aminated dextrans, protein microspheres, such as gelatin collagen and DNA etc., and bioabsorbable polymers (such as, for example, those formed from one or more of glycolide, lactide, p-dioxanone, ε-caprolactone, trimethylene carbonate, and the like). The dried, coated particles are then sprinkled as a dry powder onto a bleeding or otherwise oozing wound. Due to the coating in accordance with this disclosure, the particles absorb liquid, swell and rapidly stop the bleeding and concentrate or superconcentrate clotting factors creating clots. It is further contemplated that the present water-swellable copolymer compositions can be coated onto a sheet material (e.g., film, mesh, non-woven, foam and the like) and the coated sheet dehydrated. The dried, coated sheet can then be applied to a bleeding wound to achieve hemostasis or otherwise oozing wound to stop the oozing and assist in healing. Due to the coating in accordance with this disclosure, the sheets absorb liquid, swell and rapidly stop the bleeding.

It should also be understood that there may be applications where waiting for natural body fluids to activate the dehydrated article or coated medical device prepared in accordance with this disclosure is contraindicated. In those applications, saline or other suitable source of moisture can be provided (e.g., injected) to the site at which the article or coated medical device has been applied to tissue. In this way, the time required for full expansion of the article or coated medical device can be reduced.

EXAMPLES

Solutions of monomer containing 0.5% (w/w) HEMP and 2% (w/w) MBAA were prepared. Monomer solutions were mixed in ratios so that the total monomer concentration was 20% (w/w) in water. Two monomer solutions were combined to provide the compositions containing each monomer in amounts that varied from 25 to 75% by weight in combination as set forth in Table A. Five milliliter samples (×3) of each composition in Table A were irradiated using a UV flood lamp for anywhere from 1 to 5 minutes. Most compositions were cured in less than 30 seconds. Table A shows the average percentage weight gain for an n=3 for each composition starting from a dehydrated state at time zero.

TABLE A

| Comp† | Time in Water | KSPA-NaA | KSPA-Tris | NaA-Tris | AMPS-Tris |
|---|---|---|---|---|---|
| 25 | 10 | 873.9 | 432.95 | 202.0 | 370.3 |
| 25 | 30 | 2844.1 | 1114.2 | 308.7 | 547.7 |
| 25 | 60 | 4547.7 | 2046.9 | 437.2 | 706.2 |
| 25 | 90 | 5163.4 | 2326.0 | 1013.0 | 778.7 |
| 25 | 120 | 5552.6 | 2509.9 | 1234.0 | 823.1 |
| 50 | 10 | 511.2 | 406.9 | 239.9 | 1057.0 |
| 50 | 30 | 2794.0 | 1906.3 | 522.9 | 1543.5 |
| 50 | 60 | 5491.2 | 3374.1 | 778.2 | 1706.7 |
| 50 | 90 | 6179.9 | 3712.9 | 1450.5 | 1714.6 |
| 50 | 120 | 6422.15 | 4187.3 | 1925.7 | 1677.0 |
| 75 | 10 | 303.5 | 292.5 | 624.7 | 2677.4 |
| 75 | 30 | 778.96 | 2050.8 | 1958.3 | 3969.4 |
| 75 | 60 | 2926.5 | 4084.2 | 3729.1 | 3816.55 |
| 75 | 90 | 5933.8 | 5215.15 | 4537.1 | 3814.4 |
| 75 | 120 | 8428.9 | 6414.8 | 5146.1 | 3789.35 |

†percentage of the first of the two monomers listed. For example MEAN(KSPA-NaA) with comp = 25 refers to the 25/75 KSPA/NaA composition.

Samples were dried overnight in hood and then dried in vacuum oven over 24 hours. Swelling studies were performed to determine water gain on each sample. The study consisted of weighing each dried sample. Next, samples were placed into beakers and water was added in excess. After 10 minutes in the water, the water was drained and the samples were blot-dried using texwipes. The samples were re-weighed. The samples were placed back into the beakers, water was added. The procedure was repeated at various times of immersion in water (i.e., 30 min., 60 min., 90 min. and 120 minutes).

Rate of swelling information shows that the rate of swelling as well as the amount of total swelling depends on the copolymer composition. The AMPS-Tris compositions swelled the least of all then synthesized compositions, and showed a plateau in swelling at compositions containing more than 50% AMPS. Additionally, increasing amount of KSPA in KSPA-NaA and KSPA-Tris compositions increased the total amount of weight gain, but it did not necessarily follow that the rate of weight gain also increased. In general, KSPA-NaA>KSPA-Tris>NaA-Tris>AMPS-Tris with respect to the total amount of weight gain.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended herein.

What is claimed is:

1. A medical device comprising a composition containing a copolymer that includes a first monomer and a second monomer that is different from the first monomer, and a hydrophilicity modifying monomer, wherein both the first and second monomer are selected from the group consisting of 3-sulfopropyl acrylate potassium salt, sodium acrylate, N-(tris(hydroxyl methyl)methyl)acrylamide, and 2-acrylamido-2-methyl-1-propane sulfonic acid.

2. A medical device as in claim 1 wherein the medical device is selected from the group consisting of orthopedic pins, clamps, screws, plates clips, hooks, plugs, buttons, snaps, anchors, anastomosis rings, prosthetic devices, mandible prostheses, needles, non-permanent intrauterine devices, drug delivery devices, temporary draining, surgical instruments, vascular implants, ocular implants, burn dressings; hernia patches; absorbent swabs, gauze, sheets, felts, foams, films, gels, particles, flakes, powders, and combinations thereof.

3. A medical device as in claim 1 wherein the medical device is a hernia patch.

4. A medical device as in claim 1 wherein the composition comprises a coating on the medical device.

5. A medical device as in claim 1 wherein the composition further comprises a therapeutically beneficial compound.

6. A medical device as in claim 1 wherein the composition further comprises a contrast agent.

7. A medical device as in claim 1 wherein the composition further comprises a radioactive substance.

8. A medical device as in claim 1 wherein the composition further comprises a dye.

9. A medical device as in claim 1 wherein the composition comprises a copolymer that includes 3-sulfopropyl acrylate potassium salt and N-(tris(hydroxyl methyl)methyl)acrylamide.

10. A medical device as in claim 1 wherein the composition comprises a copolymer that includes 3-sulfopropyl acrylate potassium salt and 2-acrylamido-2-methyl-1-propane sulfonic acid.

11. A medical device as in claim 1 wherein the composition comprises a copolymer that includes 2-acrylamido-2-methyl-1-propane sulfonic acid and N-(tris(hydroxylmethyl)methyl)acrylamide.

* * * * *